United States Patent [19]
Bowen et al.

[11] Patent Number: 5,679,673
[45] Date of Patent: Oct. 21, 1997

[54] ARALKYL BRIDGED DIAZABICYCLOALKANE DERIVATIVES FOR CNS DISORDERS

[75] Inventors: Wayne Bowen, Derwood; Brian R. de Costa, Rockville; Celia Dominguez, Gaithersburg; Xiao-Shu He, Derwood; Kenner C. Rice, Bethesda, all of Md.

[73] Assignee: The United States of America, represented by the Department of Health and Human Services, Washington, D.C.

[21] Appl. No.: 344,304

[22] Filed: Nov. 21, 1994

Related U.S. Application Data

[63] Continuation of Ser. No. 950,359, Sep. 24, 1992, abandoned.
[51] Int. Cl.$^6$ ............ A61K 31/55; C07D 471/08; C07D 487/08
[52] U.S. Cl. ............ 514/221; 514/183; 514/211; 540/456; 540/460; 540/461; 540/468; 540/472; 540/477; 540/500; 540/502; 540/503; 540/552; 540/556
[58] Field of Search ............ 540/456, 460, 540/461, 468, 472, 477, 500, 502, 503, 552, 556; 514/183, 211, 221

[56] References Cited

U.S. PATENT DOCUMENTS

| 4,204,003 | 5/1980 | Szmuszkovicz | 424/324 |
|---|---|---|---|
| 4,463,013 | 7/1984 | Collins et al. | 424/274 |
| 4,801,604 | 1/1989 | Von Voightlander | 514/429 |
| 4,826,839 | 5/1989 | King et al. | 524/216 |

OTHER PUBLICATIONS deCosta, et al., "Synthesis and evaluation of optically pure [$^3$H]–(+)–pentazocine, a highly potent and selective radioligand for σ receptors", FEBS Letters 251(1,2): 53–58 (Jul. 1989).
Rodd's Chemistry of Carbon Compounds, 2nd ed., Coffey, ED., vol. IV, Part H, Chapter 37, pp. 259, 278–284–Elsevier Scientific Publishing Company (1978).
Rothman, et al., Annals of Neurology, 19(2): 105–11 (1986).
Carter, et al., J. Pharm. Exp. Ther., 247(3): 1222–1232 (1988).
Gilman, et al., The Pharmacological Basis of Therapeutics, 7$^{th}$ ed., p. 404 Macmillan (1985).
Parsons, et al., Neuropharm, 25(2): 217–220 (1986).
Lason, et al., Brain Res., 482: 333–339 (1989).
DeCosta, et al., J. Med. Chem., 32(8): 1996–2002 (1989).
Long, et al., Soc. Neurosci. Abst., 16: 1122, Abst. 461.4 (1990).
Contreras, et al., Brain Res., 546: 79–82 (1991).
Scopes, et al., J. Med. Chem., 35:490–501 (1992).
DeCosta, et al., J. Med. Chem., 35(1): 38–47 (1992).
Radesca, et al., J. Med. Chem., 34(10): 3058–65 (1991).
Cheesman, et al., Derwent Abstract WO/92128 (1992).

Giardina, Biosistemi Come Targets Farmacologici, Recettori Peptidergici, Analgesisi Oppiodi Kappa: Sintesi E Relazioni Struttura–Attivita 'Di Piperidine Sostituite, pp. 21–63 (1992).
Rees, Biosistemi Come Targets Farmacologici, Recettori Peptidergici, Synthesis & Biological Activity of Kappa–Opioid Agonists Leading to the Selection of CI-9777 (Enadoline) for Clinical Investigation, pp. 65–101 (1992).
Ronsisvalle, Biosistemi Come Targets Farmacologici, Recettori Peptidergici, Requisiti Strutturali Per I Liganti Oppioidi: E'Possible Modulare La Selecttivita, pp. 102–133 (1992).
Aram et al., J. Pharmacol. Exp. Ther., 248, 320–328 (1989) Abstract only.
Bailey et al., Eur. J. Pharmacol., 240, 243–250 (1993).
Canoll et al., J. Neurosci. Res., 24, 311–328 (1989) Abstract only.
Clissold et al., J. Pharmacol. Exp. Ther., 265, 876–886 (1993).
Cook et al., J. Pharmacol. Exp. Ther., 263, 1159–1166 (1992) Abstract only.
DeCoster et al., Brain Res., 671, 45–53, (1995) Abstract only.

(List continued on next page.)

*Primary Examiner*—Philip I. Datlow
*Attorney, Agent, or Firm*—Leydig, Voit & Mayer, Ltd.

[57] ABSTRACT

Certain aralkyl diazabicycloalkyl compounds are described for treatment of CNS disorders such as cerebral ischemia, psychoses and convulsions. Compounds of particular interest are of the formula:

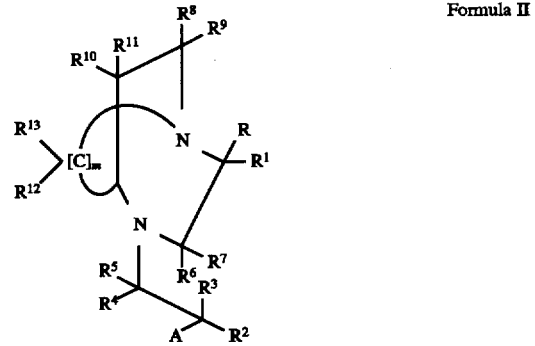

Formula II wherein each of R, $R^1$, $R^4$, $R^5$, $R^6$ and $R^7$ is independently selected from hydrido, lower-alkyl, benzyl, and haloloweralkyl; wherein each of $R^2$, $R^3$ and $R^{10}$ through $R^{13}$ is independently selected from hydrido, hydroxy, loweralkyl, benzyl, phenoxy, benzyloxy and haloloweralkyl; wherein each of $R^8$ and $R^9$ is selected from hydrido, loweralkyl, benzyl and haloloweralkyl; wherein m is an integer of from two to four; wherein A is selected from phenyl, naphthyl, benzothiophenyl, benzofuranyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

21 Claims, No Drawings

OTHER PUBLICATIONS

DeHaven-Hudkins et al., *Life Sci.*, 56, 1571–1576 (1995) Abstract only.

Gewirtz et al., *Neuropsychopharmacology*, 10, 37–40 (1994).

Itzhak et al., *FASEB J.*, 3, 1868–1872 (1989).

Kirk et al., *J. Pharmacol. Exp. Ther.*, 271, 1080–1085 (1994) Abstract only.

Klein et al., *J. Pharmacol. Exp. Ther.*, 260, 990–999 (1992) Abstract only.

Klein et al., *Eur. J. Pharmacol.*, 254, 239–248 (1994).

Lasage et al., *Synapse*, 20, 156–64 (1995) Abstract only.

Loscher et al., *Eur. J. Pharmacol.*, 238, 191–200 (1993).

Lysko et al., *Stroke*, 23, 414–419 (1992) Abstract only.

Lysko et al., *Stroke*, 23, 1319–1323 (1992) Abstract only.

Pontecorvo et al., *Brain Res. Bull.*, 26, 461–465 (1991) Abstract only.

Reddy et al., *J. Med. Chem.*, 37, 260–267, (1994) Abstract only.

Roth et al., *Eur. J. Pharmacol.*, 236, 327–331 (1993).

Takahashi et al., *Stroke*, 26, 1676–1682 (1995) Abstract only.

Tam in *Sigma Receptors*, Y. Itzhak ed., Academic Press, Harcourt Brace & Co. Publishers, London (1994) ISBN 0-12-376350-9.

Tortella et al., *Trends Pharmacol. Sci.*, 10:501–507 (1990).

Tortella et al., *Trends Pharmacol. Sci.*, 11:146–147 (1990).

Weissman et al., *Biol. Psych.*, 29, 41–54 (1991).

Witkin et al., *J. Pharmacol. Exp. Ther.*, 266, 473–482 (1993).

Rennie, "The Mice That Missed", Scientific American, Jul. 1992, pp. 20, 26.

Schnabel, Science vol. 260, Jun. 18, 1993, pp. 1719–1720.

ARALKYL BRIDGED DIAZABICYCLOALKANE DERIVATIVES FOR CNS DISORDERS

This is a continuation of application Ser. No. 07/950,359 filed Sep. 24, 1992, now abandoned.

FIELD OF THE INVENTION

This invention is in the field of clinical neurology and relates specifically to a class of therapeutically useful compounds, compositions and methods for treatment of central nervous system (CNS) dysfunctions, neurotoxic damage, or neurodegenerative diseases. For example, these compounds are particularly useful for treating neurotoxic injury which follows periods of hypoxia, anoxia or ischemia associated with stroke, cardiac arrest or perinatal asphyxia. These compounds are also useful as antipsychotics and anticonvulsants.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitetory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia-Ischemic Brain Damage," *Annals of Neurology,* 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with hypoxia, anoxia, or ischemia caused by stroke, cardiac arrest or perinatal asphyxia.

It is known that compounds of various structures, such as aminophosphonovalerate derivatives and piperidine dicarboxylate derivatives, may act as competitive antagonists at the NMDA receptor. Certain piperidineethanol derivatives, such as ifenprodil and 1-(4-chlorophenyl)-2-[1-(4-fluorophenyl)-piperidinyl]ethanol, which are known anti-ischemic agents, have been found to be non-competitive NMDA receptor antagonists [C. Carter et al, *J. Pharm Exp. Ther.,* 247 (3), 1222–1232 (1988)].

There are many classes of compounds known for treatment of psychotic disorders. For example, current therapeutic treatments for psychoses use compounds, classifiable as phenothiazine-thioxanthenes, as phenylbutylpiperidines and also as certain alkaloids. An example of a phenylbutylpiperidine compound of current use in psychotic treatment therapy is haloperidol [A. F. Gilman et al, *The Pharmacological Basis of Therapeutics,* 7th Edn., p. 404, MacMillan (1985)].

Certain nitrogen-containing cyclohetero cycloalkylaminoaryl compounds are known for pharmaceutical purposes. For example, U.S. Pat. No. 4,2204,003 to Szmuszkovicz describes N-(2-aminocyclopentyl)-N-alkanoylanilides as antidepressant agents.

Certain aminocycloaliphatic benzamides have been described for various uses. For example, U.S. Pat. No. 4,463,013 to Collins et al describes aminocyclohexylbenzamides for use as diuretic agents. The compound (+)-trans-3,4-dichloro-N-methyl-N-[2-(1-pyrrolidinyl)cyclohexyl]-benzeneacetamide has been evaluated for its selectivity as an amino acid antagonist [C. G. Parsons et al, *Neuropharm.,* 25(2), 217–220 (1986)]. This same compound has been evaluated for its neuroprotective activity against kainate-induced toxicity [W. Lason et al, *Brain Res.,* 482, 333–339 (1989)]. U.S. Pat. No. 4,801,604 to Vonvoightlander et al describes certain cis-N-(2-aminocycloaliphatic)benzamides as anticonvulsants including, specifically, the compound cis-3,4-dichloro-N-methyl-N-[2-(1-pyrrolidinyl)cyclohexyl]benzamide. Certain of these trans benzeneacetamide derivatives, such as trans-3,4-dichloro-N-methyl-N-[2-(1-pyrrolidinyl)cyclohexyl]-benzeneacetamide, have been described as highly selective ligands for kappa opioid receptors. The cis isomers of 3,4-dichloro-N-methyl-N-[2-(1-pyrrolidinyl)cyclohexyl]-benzeneacetamide were identified to be potent and selective sigma ligands [B. R. de Costa et al, *J. Med. Chem.,* 32(8), 1996–2002 (1989)]. Further structure activity studies with these compounds resulted in the identification of (+)- and (−)-cis-N-[3,4-dichlorophenylethyl]-N-methyl-2-(1-pyrrolidinyl)-cyclohexylamines as extremely potent and selective ligands for the sigma receptor. These [Contreras, P. C.; Ragan, D. M.; Bremer, M. E.; Lanthorn, T. H.; Gray, N. M.; Iyengar, S.; Jacobson, A. E.; Rice, K. C.; de Costa, B. R.: Evaluation of U50488H analogs for antiischemic activity in the gerbil. *Brain Res.* 1991, 546, 79–82] and related (ethylenediamines) compounds [Long, J. B.; Tortella, F. C.; Rice, K. C.; de Costa B. R.: Selective sigma ligands protect against dynorphin A-induced spinal cord injury in rats. *Soc. Neurosci. Abs.,* 16, 1122 (1990) abs 461.4] were found to be effective as protective agents for the damaging effects of ischemia and stroke in two different models of ischemia. See, for example, Long, J. B.; Tortella, F. C.; Rice, K. C.; de Costa B. R.: Selective sigma ligands protect against dynorphin A-induced spinal cord injury in rats. *Soc. Neurosci. Abs.,* 16, 1122 (1990) abs 461.4; Contreras, P. C.; Ragan, D. M.; Bremer, M. E.; Lanthorn, T. H.; Gray, N. M.; Iyengar, S.; Jacobson, A. E.; Rice, K. C.; de Costa, B. R.: Evaluation of U50488H analogs for antiischemic activity in the gerbil. *Brain Res.* 1991, 546, 79–82. Since these initial findings, neuroprotective activity has been identified among certain other high affinity sigma ligands. It is likely that the protective effects of these and related compounds is mediated through their interaction with the sigma receptor. Scopes et al., *J. Med. Chem.,* 35, 490–501 (1992) describe certain 2-[(alkylamino)methyl]-piperidines. In particular, 1-[(3,4-dichlorophenyl)acetyl]-2[(alkylamino)methyl]piperidines are described as having activities as kappa opioid receptor agonists.

BRIEF DESCRIPTION OF THE INVENTION

Treatment of CNS disorders and diseases such as cerebral ischemia, psychotic disorders and convulsions, as well as prevention of neurotoxic damage and neurodegenerative diseases, may be accomplished by administration of a therapeutically-effective amount of a compound of the formula:

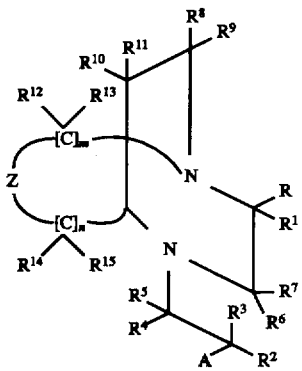

Formula I wherein each of R, $R^1$, $R^4$, $R^5$, $R^6$ and $R^7$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein each of $R^2$, $R^3$ and $R^{10}$ through $R^{15}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein each of $R^8$ and $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein R and $R^1$ may be taken together to form oxo or to form a saturated or partially unsaturated carbocyclic group having three to eight ring carbons; wherein $R^2$ and $R^3$ may be taken together to form oxo or to form a saturated or partially unsaturated carbocyclic group having three to eight ring carbons; wherein $R^4$ and $R^5$ may be taken together to form oxo or to form a saturated or partially unsaturated carbocyclic group having three to eight ring carbons; wherein $R^{12}$ and $R^{13}$ may be taken together to form oxo; wherein $R^{14}$ and $R^{15}$ may be taken together to form oxo; wherein each of m and n is an integer of from one to four; wherein Z is selected from O, S, >N-$R^{16}$, 'SO, >SO$_2$,

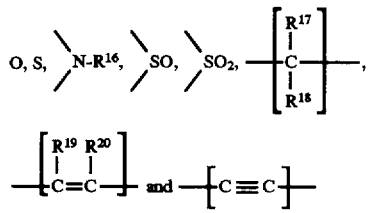

wherein $R^{16}$ is selected from hydrido, alkyl, cycloalkyl, cycloalkylalkyl, aryl, aralkyl, heteroaryl, alkanoyl, aralkanoyl, aroyl, aminoalkyl, monoalkylaminoalkyl and dialkylaminoalkyl; wherein each of $R^{17}$ and $R^{18}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein each of $R^{19}$ and $R^{20}$ is independently selected from hydrido, alkyl, cycloalkyl, cycloalkylalkyl, aralkyl, alkoxyalkyl, haloalkyl, hydroxyalkyl, halo, cyano, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically-acceptable salt thereof.

A preferred family of compounds of Formula I consists of those compounds wherein each of R, $R^1$, $R^4$, $R^5$, $R^6$ and $R^7$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein each of $R^2$, $R^3$ and $R^{10}$ through $R^{15}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein each of $R^8$ and $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein R and $R^1$ my be taken together to form oxo or to form a saturated or partially unsaturated carbocyclic group having three to eight ring carbons; wherein $R^2$ and $R^3$ may be taken together to form oxo or to form a saturated or partially unsaturated carbocyclic group having three to eight ring carbons; wherein $R^4$ and $R^5$ may be taken together to form oxo or to form a saturated or partially unsaturated carbocyclic group having three to eight ring carbons; wherein $R^{12}$ and $R^{13}$ may be taken together to form oxo; wherein $R^{14}$ and $R^{15}$ may be taken together to form oxo; wherein each of m and n is an integer from one to four;

wherein Z is selected from O, >N—$R^{16}$,

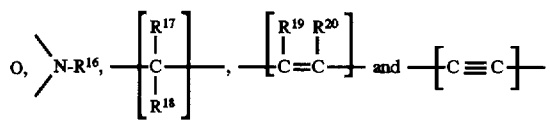

wherein $R^{16}$ may be selected from hydrido, alkyl, cycloalkyl, cycloalkylalkyl, aryl, aralkyl, heteroaryl, alkanoyl, aralkanoyl and aroyl; wherein each of $R^{17}$ through $R^{20}$ is independently selected from hydrido, alkyl, cycloalkyl, cycloalkylalkyl, aralkyl, aryl, alkoxyalkyl, haloalkyl, hydroxyalkyl, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

A more preferred family of compounds within Formula I consists of those compounds wherein each of R, $R^1$, $R^4$, $R^5$, $R^6$ and $R^7$ is independently selected from hydrido, loweralkyl, cycloalkyl of three to about eight carbon atoms, phenylloweralkyl, phenyl, loweralkoxyloweralkyl, haloloweralkyl; hydroxyloweralkyl, carboxy, carboxyloweralkyl, loweralkanyl, loweralkenyl, loweralkynyl; wherein $R^2$, $R^3$ and $R^{10}$ through $R^{15}$ is independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, haloloweralkyl, hydroxyloweralkyl, cyano, amino, monoloweralkylamino, diloweralkylamino, carboxy, carboxyloweralkyl, loweralkanoyl, loweralkenyl and loweralkynyl; wherein each of $R^8$ and $R^9$ is independently selected from hydrido, loweralkyl, cycloalkyl of three to about eight carbon atoms, phenylloweralkyl, phenyl, loweralkoxyloweralkyl, haloloweralkyl, hydroxyloweralkyl, carboxy, carboxyloweralkyl, loweralkanoyl, loweralkenyl and loweralkynyl; wherein $R^2$ and $R^3$ may be taken together to form a saturated or partially unsaturated carbocyclic group having three to eight ring carbons; wherein $R^4$ and $R^5$ may be taken together to form a saturated or partially unsaturated carbocyclic group having three to eight ring carbons; wherein $R^{12}$ and $R^{13}$ may be taken together to form oxo; wherein $R^{14}$ and $R^{15}$ may be taken together to form oxo; wherein m is an integer from 2–4 and n and p are integers of from one to four;
wherein Z is selected from O, $>$N—$R^{16}$,

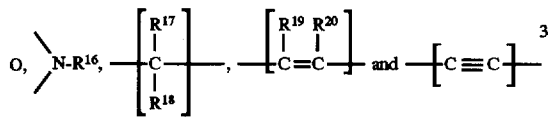

wherein $R^{16}$ may be selected from hydrido, loweralkyl, cycloalkyl of three to about eight carbon atoms, cycloalkylalkyl of four to about eight carbon atoms, phenyl, phenylloweralkyl, heteroaryl, loweralkanoyl, phenylalkanoyl, benzoyl, aminoloweralkyl, monoloweralkyl-aminoloweralkyl and diloweralkylaminoloweralkyl; wherein each of $R^{17}$ and $R^{18}$ is independently selected from hydrido, hydroxy, loweralkyl, cycloalkyl of three to about eight carbon atoms, cycloalkylalkyl of four to about eight carbon atoms, phenyloweralkyl, phenyl, loweralkoxyloweralkyl, haloloweralkyl, hydroxyloweralkyl, halo, cyano, amino, monoloweralkylamino, diloweralkylamino, carboxy, carboxyloweralkyl and loweralkanoyl; wherein each of $R^{19}$ and $R^{20}$ is independently selected from hydrido, loweralkyl, cycloalkyl of three to about eight carbon atoms, cycloalkylalkyl of four to about eight carbon atoms, phenylloweralkyl, phenyl, loweralkoxyloweralkyl, haloloweralkyl, hydroxyloweralkyl, halo, cyano, carboxy, carboxyloweralkyl and loweralkanoyl; wherein A is selected from phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, naphthylloweralkylamino, heteroaralkylamino, phenylthio, naphthylthio, heteroarylthio, phenylloweralkylthio and heteroarylloweralkylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

A more highly preferred family of compounds of Formula I consists of those-compounds wherein each of R, $R^1$, $R^4$, $R^5$, $R^6$ and $R^7$ is independently selected from hydrido, loweralkyl, cycloalkyl of three to about eight carbon atoms, cycloalkylalkyl of four to about eight carbon atoms, benzyl, phenyl, loweralkoxyloweralkyl, haloloweralkyl, hydroxyloweralkyl, loweralkanoyl, loweralkenyl, and loweralkynyl; wherein $R^2$, $R^3$ and $R^{10}$ through $R^{15}$ is independently selected from hydrido, hydroxy, loweralkyl, cycloalkyl of three to about eight carbon atoms, cycloalkylalkyl of four to about eight carbon atoms, benzyl, phenyl, loweralkoxy, phenoxy, benzyloxy, loweralkoxyloweralkyl, haloloweralkyl, hydroxyloweralkyl, loweralkanoyl, loweralkenyl and loweralkynyl; wherein each of $R^8$ and $R^9$ is independently selected from hydrido, loweralkyl, cycloalkyl of three to about eight carbon atoms, phenylloweralkyl, phenyl, loweralkoxyloweralkyl, haloloweralkyl, hydroxyloweralkyl, carboxy, carboxyloweralkyl, loweralkanoyl, loweralkenyl and loweralkynyl; wherein $R^2$ and $R^3$ may be taken together to form a saturated or partially unsaturated carbocyclic group having three to eight ring carbons; wherein $R^4$ and $R^5$ may be taken together to form a saturated or partially unsaturated carbocyclic group having three to eight ring carbons; wherein $R^{12}$ and $R^{13}$ may be taken together to form oxo; wherein each of m and n is an integer of from one to four;
wherein Z is selected from O, $>$N—$R^{16}$,

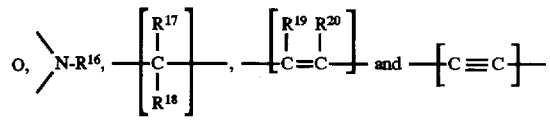

wherein $R^{16}$ may be selected from hydrido, loweralkyl, cycloalkyl of three to about eight carbon atoms, cycloalkylalkyl of four to about eight carbon atoms, phenyl and benzyl; wherein each of $R^{17}$ through $R^{20}$ is independently selected from hydrido, loweralkyl, cycloalkyl of three to about eight carbon atoms, cycloalkylalkyl of four to about eight carbon atoms, benzyl, phenyl, loweralkoxyloweralkyl, hydroxyloweralkyl and halo; wherein A is selected from phenyl, naphthyl, benzo[b]thienyl, thienyl, phenoxy, benzyloxy, naphthyloxy, thiophenoxy, phenylamino, benzylamino, naphthylamino, phenylthio, benzylthio and naphthylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

A family of compounds of particular interest within Formula I are compounds embraced by Formula II:

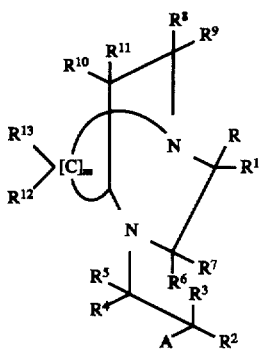

Formula II wherein each of R, $R^1$, $R^4$, $R^5$, $R^6$ and $R^7$ is independently selected from hydrido, loweralkyl, benzyl and halolower-alkyl; wherein each of $R^2$, $R^3$ and $R^{10}$ through $R^{13}$ is independently selected from hydrido, hydroxy, loweralkyl, benzyl, phenoxy, benzyloxy and haloloweralkyl; wherein each of $R^8$ and $R^9$ is independently selected from hydrido, loweralkyl, benzyl and haloloweralkyl; wherein m is an integer of from two to four; wherein A is selected from phenyl, naphthyl, benzothienyl, benzofuranyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

A more preferred family of compounds within Formula II consists of compounds wherein each of R, $R^1$, $R^4$, $R^5$, $R^6$ and $R^7$ is independently selected from hydrido, methyl, ethyl, propyl, benzyl, and haloloweralkyl, wherein each of $R^2$, $R^3$ and $R^{10}$ through $R^{13}$ is independently selected from hydrido, hydroxy, methyl, ethyl, propyl, benzyl, phenoxy, benzyloxy and haloloweralkyl; wherein each of $R^8$ and $R^9$ is independently selected from hydrido, methyl, ethyl, propyl, benzyl and haloloweralkyl; wherein m is an integer of from two or three; wherein A is phenyl or naphthyl; wherein any of the foregoing A groups can be further substituted with one or more substituents independently selected from hydroxy, methyl, ethyl, propyl, methoxy, ethoxy, methylenedioxy, halo, trifluoromethyl, amino, methylamino and dimethylamino; or a pharmaceutically acceptable salt thereof.

Of highest interest are the following specific compounds:
4-[2-(3,4-dichlorophenyl)ethyl]1,4-diazabicyclo[2.2.3]nonane;
4-[2-(3-benzothienyl)ethyl]-1,4-diazabicyclo[2.2.3]nonane;
4-[2-naphthylethyl]-1,4-diazabicyclo[2.2.3]nonane;
4-[2-(3,4-dichlorophenyl)ethyl-1,4-diazabicyclo[3.2.3]decane;
4-[2-(3-benzothienyl)ethyl]-1,4-diazabicyclo[4.2.3]undecane;
4-[2-naphthylethyl]-1,4-diazabicyclo[5.2.3]dodecane;

The term "hydrido" denotes a single hydrogen atom (H) which may be attached, for example, to an oxygen atom to form hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about six carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. An example of a polyhaloalkyl is a trifluoromethyl group. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably two to about ten carbon atoms, and containing at least one carbon-carbon double bond. The term "alkynyl" embraces linear or branched radicals having two to about twenty carbon atoms, preferably two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl including benz-fused systems such as benzothienyl, 2-quinolinyl and the like. The term "alkylene chain" describes a chain of two to six methylene (—$CH_2$—) groups which may form a cyclic structure with or without a hetero atom in the cyclic structure.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neo-pentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formulas I–II are the tautomeric forms of the described compounds, isomeric forms including enantiomers and diastereoisomers, and the pharmaceutically-acceptable salts thereof. The term "pharmaceutically-acceptable salts" embraces salts commonly used to form alkali metal salts and to form addition salts of free acids or free bases. Since the compounds of Formulas I–II contain basic nitrogen atoms, such salts are typically acid addition salts. The phrase "pharmaceutically-acceptable salts" is not intended to embrace quaternary ammonium salts. The nature of the salt is not critical, provided that it is pharmaceutically acceptable, and acids which may be employed to form salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I–II in a suitable solvent (e.g. methanol).

General Synthetic Procedures

Compounds of Formulas I and II may be prepared in accordance with the following generic procedures, within which specific schemes are shown for Formula II type compounds.

Step 1

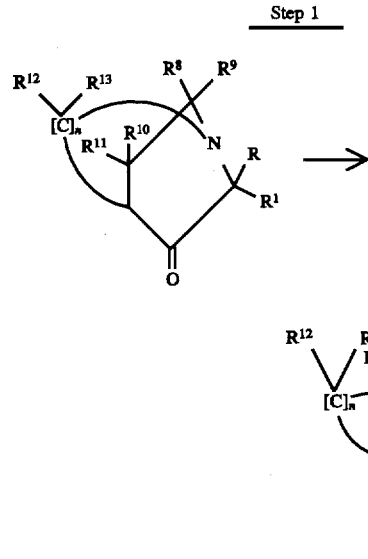

wherein R, $R^1$, $R^8$ through $R^{13}$, and n are as defined previously.

A process for preparing the compounds of the invention starts with an oxo derivative of a bridged azabicycloalkane of general structure 1 where R, $R^1$, $R^8$ through $R^{13}$, and n have the value assigned previously. An examples of a compound within the general structure 1 is 3-quinuclidone. The salt, e.g. hydrochloride, of 1 is converted to the corresponding oxime with hydroxylamine hydrochloride and sodium acetate in a suitable solvent, e.g. ethanol. The reaction can be conducted over a wide temperature range such as from room temperature to reflux.

Step 2

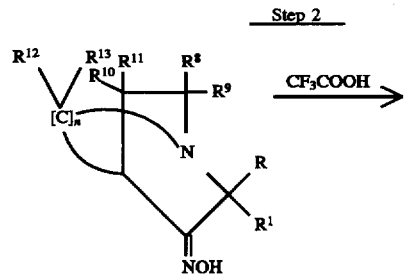

-continued
Step 2

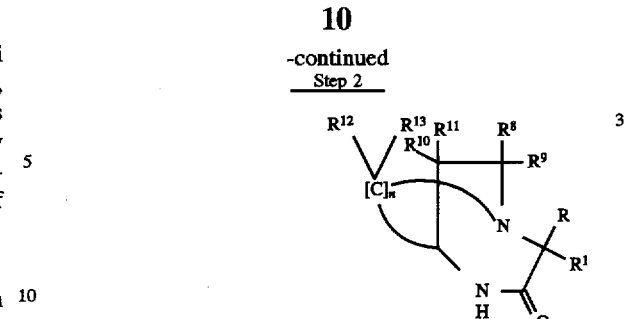

wherein R, $R^1$, $R^8$, $R^9$, $R^{10}$, $R^{11}$, $R^{12}$, $R^{13}$ and n are as defined previously.

In the second step of the process, compounds of the general formula 2 are converted to the corresponding 3-keto-1,4-diazabicycloalkane derivative 3. This conversion is achieved by reacting a compound of formula 2 with an acid, such as trifluoroacetic acid.

Step 3

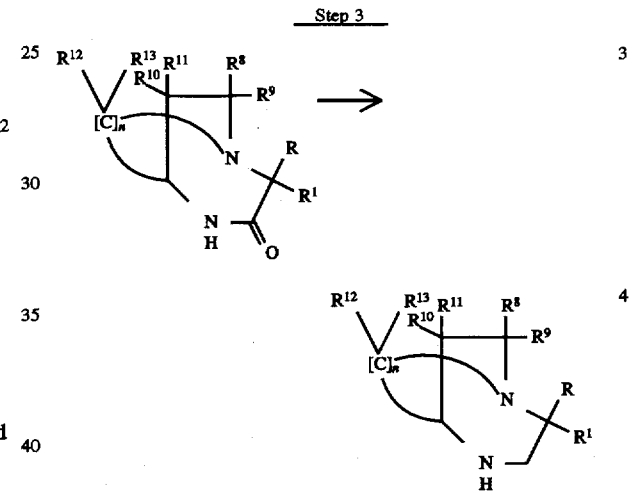

wherein R, $R^1$, $R^8$, $R^9$, $R^{10}$, $R^{11}$, $R^{12}$, $R^{13}$ and n are as defined previously. In the third step of the process, compounds of general structure 3 are treated with a reducing agent such as lithium aluminum hydride in a suitable solvent such as tetrahydrofuran. The resulting product 4 is a diazabicycloalkane.

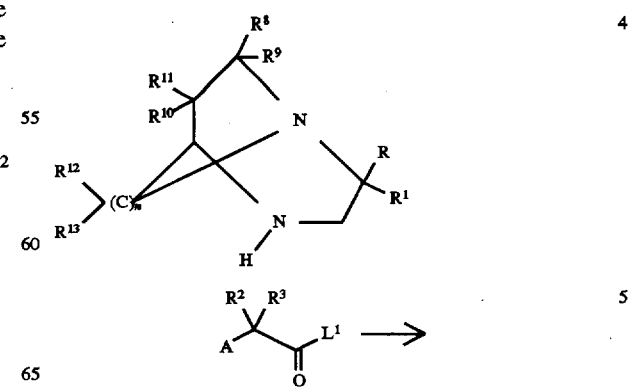

-continued

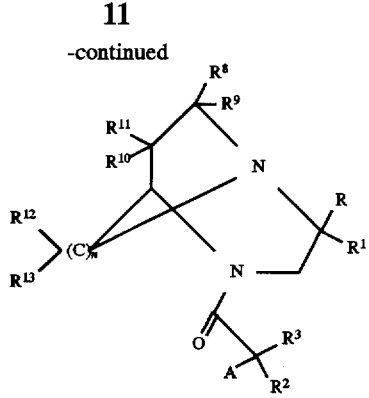
6 wherein A, R, $R^1$, $R^2$, $R^3$, $R^8$ through $R^{13}$ and n are as defined previously; and wherein $L^1$ is a good leaving group such as chloro, bromo, acyloxy, or "activated" hydroxy.

In the fourth step of the process, diazabicycloalkanes of general structure 4 are converted to amides of general structure 6 where A, $R^2$, and $R^3$ have the value assigned previously and $L^1$ is a good leaving group such as chloro, bromo, acyloxy, or "activated" hydroxy. The conversion can be best achieved by mixing the reagents neat or in an aprotic solvent such as tetrahydrofuran, methylene chloride, or ether in the presence of a base such as triethylamine. The reaction can be run in the absence or presence of an activating agent such as dicyclohexylcarbodiimide or phosphorus oxychloride, depending on the leaving group of choice. The temperature of the reaction can vary from 0° to reflux of the reaction mixture.

Step 5

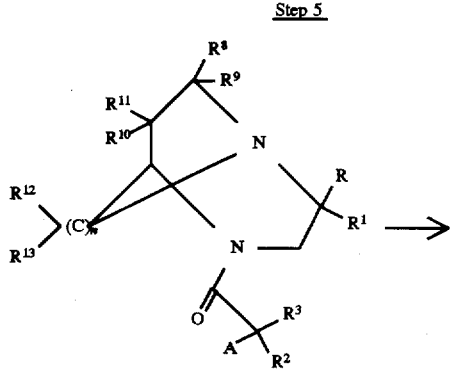
6

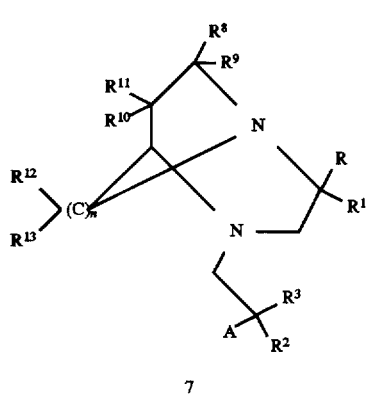
7 wherein A, R, $R^1$, $R^2$, $R^3$, $R^8$ through $R^{13}$ and n are as defined previously.

In the fifth step of the process, amides of general structure 6 are converted to amines of general structure 7 by employing reducing agents such as lithium aluminum hydride, aluminum hydride, sodium borohydride, sodium cyanoborohydride, or .Other reducing agents familiar to those skilled in the art. This reduction can be accomplished in either protic or aprotic solvents, depending on the reducing agent of choice, and at temperatures ranging from room temperature to reflux of the reaction mixture.

Alternately, amines of general structure, 9 can be prepared according to the following generic procedure:

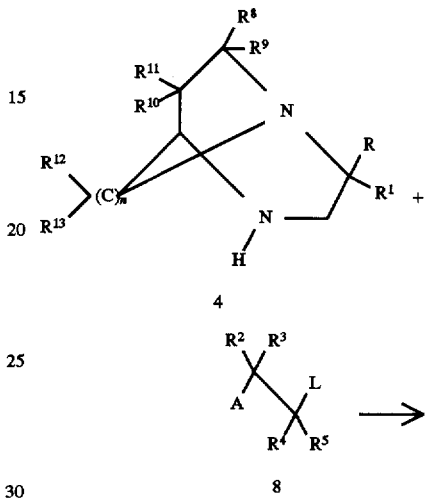
4
8

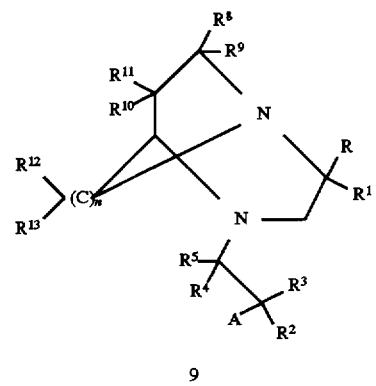
9 wherein A, $R^1$ through $R^5$, $R^8$ through $R^{13}$ and m and n are as defined previously; and wherein $L^2$ is a good leaving group such as halogen, tosylate, mesylate, or brosylate.

The compounds can be combined in a variety of solvents such as toluene, xylenes, dimethylformamide, hexamethylphosphoramide, or ethanol. The temperature of the reaction can vary from room temperature to reflux of the reaction mixture.

The schemes set forth below illustrate in more detail the above general method for preparing aralkyl diazabicycloalkanes of the present invention.

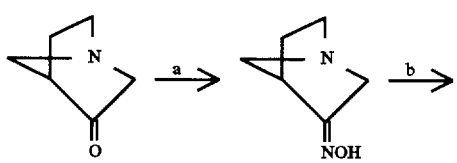

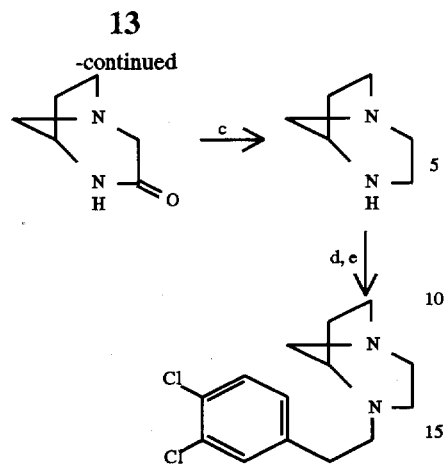

a: HONH$_2$·HCl, NaOAc, EtOH, r.t.; b: CF$_3$COOH; c: LiAlH$_4$, THF; d: 3,4-dichlorophenylacetic acid, DCC, CH$_2$Cl$_2$, r.t.; e: AlH$_3$, THF, r.t.

The following Examples are detailed descriptions of the methods of preparation of compounds of Formula I. These detailed preparations fall within the scope of, and serve to exemplify, the above described Generic Procedures which form part of the invention. These Examples are presented for illustrative purposes only and are not intended as a restriction on the scope of the invention. All parts are by weight unless otherwise indicated. Most of the commercially available starting materials were obtained from Aldrich Chemical Company, Milwaukee, Wis.

Melting points were determined on a Thomas-Hoover capillary apparatus and are uncorrected. Specific rotation determinations at the sodium-D line were obtained in a 1 dM cell using a Perkin-Elmer 241-MC polarimeter. Elemental analyses were performed at Atlantic Microlabs, Atlanta, Ga. Chemical-ionization mass spectra (CIMS) were obtained using a Finnigan 1015 mass spectrometer. Electron ionization mass spectra (EIMS) and high resolution mass measurements (HRMS) were obtained using a VG-Micro Mass 7070F mass spectrometer. $^1$H-NMR spectra were measured from CDCl$_3$ solutions using a Varian SL-300 spectrometer. Thin layer chromatography (TLC) was performed on 250 µM Analtech GHLF silica gel plates.

EXAMPLE 1

Preparation of 3-Quinuclidone oxime

To a stirred solution of 3-quinuclidone HCl (75 g, 663 mmol) and NH$_2$OH.HCl (38.7 g, 557 mmol, 1.2 eq) in EtOH (1000 mL) was added NaOAc.3H$_2$O (189.4 g, 1.39 mole, 3.0 eq) and the reaction mixture was stirred overnight at room temperature when TLC (1:9:90 concentrated aqueous ammonia —MeOH—CHCl$_3$1:9:90) indicated complete reaction. The solvent was evaporated in vacuo and the residue was dissolved in water (800 mL) and K$_2$CO$_3$ was added to pH=10 when a copious suspension of the 3-quinuclidone oxime base formed. The aqueous mixture was filtered and the filter cake was washed 3 times with cold water and oven dried in vacuo to give 65.8 g (100%) of 45 as a colorless solid. Crystallization from EtOH (300 mL) afforded the title compound (52.0 g, 80%): mp 117°–119 ° C.; $^1$H-NMR (CDCl$_3$) δ 8.93 (brs, 1H.NOH), 3.66 (s, 2H), 2.92 (m, 4H), 2.59 (t, J=0, 3.2 Hz, 1H), 1.81 (m, 4H); Anal (calcd for C$_7$H$_{12}$N$_2$O): C 59.98, H 8.63, N 19.98. Found: C 60.14, H 8.60, N 20.04.

EXAMPLE 2

Preparation of 3-Keto-1,4-diazabicyclo[2.2.3]-nonane

The title compound of Example 1 (10 g, 71.4 mmol) in a 250 mL rb flask was treated with CF$_3$COOH (30 mL) with stirring. The solution became hot and then became viscous as it cooled to room temperature. TLC (1:9:90 concentrated aqueous ammonia —MeOH—CHCl$_3$ 1:9:90) indicated the reaction to be 95% complete after 10 minutes at room temperature. After 1 hour, reaction was complete. The reaction mixture was poured into a solution of K$_2$CO$_3$ (67 g) in water (200 mL) and extracted with CHCl$_3$ (4×200 mL). The combined organic extract was dried (Na$_2$SO$_4$) and the solvent was evaporated in vacuo to give the title compound (9.4 g, 96%) as a white crystalline solid. Recrystallization from hot 2-propanol (80 mL) afforded 7.90 g (79%): mp 218°–219° C.; $^1$H-NMR (CDCl$_3$) δ 8.40 (br s, 1H, CONH), 3.66 (s, 2H), 2.78–3.03 (m, 4H), 2.59 (m, 1H), 1.81 (m, 4H); Anal (calcd for C$_7$H$_{12}$N$_2$O): C 59.98, H 8.63, N 19.98. Found: C 60.07, H 8.60, N 20.07.

EXAMPLE 3

Preparation of 1,4-Diazabicyclo[2.2.3]nonane

The title compound of Example 2 (1.70 g, 12.1 mmol) was added portionwise at room temperature to a stirred solution of AlH$_3$ (60 mL of a 1.0M solution, 60 mmol). The solution became warm. Stirring was continued for a further 20 minutes and the reaction mixture was poured into cold (5° C.) 30% aqueous KOH solution (100 mL) and the aqueous mixture was extracted with CHCl$_3$ (200 mL). The organic extract was dried (Na$_2$SO$_4$) and evaporated to give the title compound in quantitative yield: mp 250° C. (dec) (EtOH); $^1$H-NMR (CDCl$_3$) δ 3.02–3.25 (m, 1H), 2.66–3.02 (complex m, 3H), 2.59 (m, 1H), 2.43 (m, 1H), 2.25–2.40 (m, 1H), 1.87 (m, 1H), 1.04–1.77 (complex m, 6H); Anal (calcd for C$_{17}$H$_{16}$Cl$_2$N$_2$·0.33H$_2$O): C 40.99, H 8.19, N 13.66. Found C 41.00, H 8.31, N 13.68.

EXAMPLE 4

Preparation of 4-(3,4-Dichlorophenylacetyl)-1,4-diazabicyclo[2.2.3]nonane

The title compound of Example 3 HCl salt of the (1.5 g, 7.56 mmol) was coupled with 3,4-dichlorophenylacetic acid (2.32 g, 11.3 mmol) in the presence of 1,3-dicyclohexylcarbodiimide (3.11 g, 15.1 mmol, 2.0 eq) and triethylamine (2.29 g, 3.0 eq) in CH$_2$C$_{12}$ (50 ml). After stirring overnight at room temperature, the reaction mixture was filtered and the filter-cake was washed with a little (25 ml) of ether. The combination filtrate and washings were washed with 10% citric acid (100 ml) and the organic layer was discarded. The citric acid layer was washed with ether (2×50 ml) and then basified (to pH 9.5) with excess concentrated aqueous NH$_3$ solution. Extraction with CH$_2$Cl$_2$ (50 ml) drying (Na$_2$SO$_4$) and evaporation of the solvent afforded the product as an oil which was converted to the oxalate salt (0.64 g, 21%) mp 180°–182° C. (2-propanol); $^1$H-NMR (CDCl$_3$) δ 7.43 (d, J=8.3 Hz, 1H), 7.39 (d, J=2.1 Hz, 1H), 7.13 (dd, J=2.1, 8.3 Hz, 1H), 5.52 (br s, 1H), 3.94 (m, 1H), 3.51 (s, 2H), 3.32 (m, 1H), 2.67–2,91 (m, 4H), 2.37 (ddd, J=2.0, 4.9, 14 Hz, 1H), 1.88 (q, J$_{app}$=3.1 Hz, 1H), 1.59–1.68 (m, 2H), 1.45 (m, 2H); Anal (calcd for C$_{17}$H$_{20}$Cl$_2$N_2O$_5$): C 50.63, H 5.00, N 6.95. Found: C 50.64, H 5.12, N 6.65.

EXAMPLE 4

Preparation of 4-[2-(3,4-Dichlorophenyl)ethyl]-1,4-diazabicyclo[2.2.3]nonane (16) , The title compound of Example 4 (0.39 g, 1.24 mmol) was reduced with 1.0M AlH$_3$ in THF as described in Example 3 to give the fumarate of the title compound (0.30 g, 45%): mp 167°–168° C. (2-propanol); $^1$H-NMR (CDCl$_3$) δ 7.36 (d, J=8.3 Hz, 1H), 7.32 (d, J=2.0 Hz, 1H), 7.05 (dd, J=2.0, 8.3 Hz, 1H), 3.11 (m, 1H), 2.65–2.91 (complex m, 8H), 2.36 (dm, J=14 Hz, 1H), 1.19–1.84 (complex m, 7H); Anal (calcd for C$_{23}$H$_{28}$Cl$_2$N$_2$O$_8$): C 51.99, H 5.31, N 5.27. Found C 53.17, H 5.55, N 5.36.

Biological-Evaluation

Radioreceptor Assay

The compound of Example 5 was tested for its ability to displace [$^3$H](+)-pentazocine from guinea pig brain membranes [de Costa et al, *FEBS Lett.*, 251, 53–58, 1989] to determine the relative potency of the compounds interacting with the sigma receptor. Receptor binding assays were performed using the crude synaptosomal (P$_2$) membrane fraction of guinea pig brain.

Crude P$_2$ membrane fractions were prepared from frozen (–80° C.) guinea pig brains (Pel-Freeze, Rogers, Ak.), minus cerebella. After removal of cerebella, brains were allowed to thaw slowly on ice and placed in ice-cold 10 mM Tris-HCl, pH 7.4, containing 320 mM sucrose (Tris-sucrose buffer). Brains were then homogenized in a Potter-Elvehjem homogenizer by 10 strokes of a motor driven Teflon pestle in a volume of 10 mL/g tissue wet weight. The homogenate was centrifuged at 1000 g for 10 min at 4° C., and the supernatants were saved. The pellets were resuspended by vortexing in 2mL/g ice-cold Tris-sucrose and centrifuged again at 1000 g for 10 min. The combined 1000 g supernatant was centrifuged at 31000 g for 15 min at 4° C. The pellets were resuspended by vortexing in 3 mL/gm of 10 mM Tris-HCl, pH 7.4, and the suspension was allowed to incubate at 25° C. for 15 min. Following centrifugation at 31000 g for 15 min, the pellets were resuspended by gentle Potter-Elvehjem homogenization to a final volume of 1.53 mL/g in 10 mM Tris-HCl, pH 7.4. Aliquots were stored at –80° C. until use. Protein concentration was determined by the method of Lowry et al. [Lowry et al, *J. Biol. Chem.*, 193, 265–271, 1951] using bovine serum albumin (BSA) as standard.

To prepare rat brain crude P$_2$ membranes, male Sprague-Dawley rats (150–200 g, Charles River, Boston, Mass.) were sacrificed by decapitation. Brains (minus cerebella) were then treated as described above. &

Each compound was initially screened at concentrations of 10, 100, and 1000 nM in order to obtain an estimate of sigma binding affinity and to determine the appropriate concentration range to use in 12-point competition curves. For most compounds in the study, a concentration range of 0.0005–100 nM was appropriate. A range of 0.005–1000 nM or 0.05–10,000 nM was used for the less potent compounds. Twelve concentrations of unlabeled ligand were incubated with 3 nM [$^3$H](+)-pentazocine as described previously [de Costa et al, *FEBS Lett.*, 251, 53–58, 1989]. The CDATA iterative curve-fitting program (EMF Software, Inc., Baltimore, Md.) was used to determine IC$_{50}$ values. Values are the average of 2–4 experiments ±SEM. Each experiment was carried out in duplicate. The Cheng-Prussoff equation [Cheng, Y. C. and Prusoff, W. H., *Biochem. Pharmacol.*, 22, 3099–3108, 1973] was then used to convert IC$_{50}$ values to apparent K$_i$ values. The K$_d$ for [$^3$H]-(+)-pentazocine (4.8 nM) was determined in independent experiments using guinea pig brain membranes.

Sigma receptors were labeled with [$^3$H]-(+)-pentazocine (Specific activity=51.7 Ci/mmol). Incubations were carried out in 50 mM Tris-HCl, pH 8.0, for 120 min at 25° C. in a volume of 0.5 mL with 500 μg of membrane protein and 3 nM [$^3$H]-(+)-pentazocine. Nonspecific binding was determined in the presence of 10 μM (+)-pentazocine. Assays were terminated by the addition of 5 mL of ice-cold 10 mM Tris-HCl, pH 8.0, and filtration through glass-fiber filters (Schleicher and Schuell). Filters were then washed twice with 5 mL of ice-cold Tris-HCl buffer. Filters were soaked in 0.5% polyethylenimine for at least 30 min at 25° C. prior to use.

TABLE II

| Test Compound | Ki ([3H] (+) -Pent) nM |
|---|---|
| Compound of Ex. 5 | 125 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical compositions may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, aqueous sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound belonging to the family of compounds as set forth in the following formula:

wherein:

n is an integer from 2 to 5;

R, $R^1$, $R^4$, $R^5$, $R^6$ and $R^7$ are independently selected from the group consisting of hydrido, loweralkyl, haloloweralkyl, and benzyl;

$R^2$, $R^3$, and $R^{10}$ through $R^{13}$ are independently selected from the group consisting of hydrido, hydroxy, loweralkyl, haloloweralkyl, benzyl, phenoxy, and benzyloxy;

$R^8$ and $R^9$ are independently selected from the group consisting of hydrido, loweralkyl, haloloweralkyl and benzyl; and A is selected from the group consisting of phenyl, naphthyl, benzothienyl, benzofuranyl, and thienyl, wherein any of the foregoing A groups can be further substituted with one or more substituents independently selected from hydrido, hydroxy, halo, loweralkyl, haloloweralkyl, loweralkoxy, amino, monoloweralkylamino, and diloweralkylamino;

or a pharmaceutically acceptable salt thereof.

2. The compound of claim 1 wherein:

n is an integer of from 2 to 5;

R, $R^1$, $R^4$, $R^5$, $R^6$ and $R^7$ are each independently selected from the group consisting of hydrido, methyl, ethyl, propyl, haloloweralkyl, and benzyl;

$R^2$, $R^3$, and $R^{10}$ through $R^{13}$ are each independently selected from the group consisting of hydrido, hydroxy, methyl, ethyl, propyl, haloloweralkyl, benzyl, phenoxy, and, benzyloxy;

$R^8$ and $R^9$ are each independently selected from the group consisting of hydrido, methyl, ethyl, propyl, haloloweralkyl, and benzyl;

A is selected from the group phenyl or naphthyl; wherein any of the foregoing A groups can be further substituted with one or more substituents independently selected from the group consisting of hydroxy, methyl, ethyl, propyl, methoxy, ethoxy, methylenedioxy, halo, trifluoromethyl, amino, methylamino and dimethylamino;

or a pharmaceutically acceptable salt thereof.

3. The compound of claim 2, wherein the compound is selected from the group consisting of:

4-[2-(3,4-dichlorophenyl)ethyl]-1,4-diazabicyclo[2.2.3]nonane;

4-[2-(3-benzothienyl)ethyl]-1,4-diazabicyclo[2.2.3]nonane;

4-[2-naphthylethyl]-1,4-diazabicyclo[2.2.3]nonane;

4-[2-(3,4-dichlorophenyl)ethyl]-1,4-diazabicyclo[3.2.3]decane;

4-[2-(3-benzothienyl)ethyl]-1,4-diazabicyclo[4.2.3]undecane; and

4-[2-naphthylethyl]-1,4-diazabicyclo[5.2.3]dodecane.

4. The compound of claim 3 which is 4-[2-(3,4-dichlorophenyl)ethyl]-1,4-diazabicyclo[2.2.3]nonane.

5. The compound according to claim 3 which is 4-[2-(3-benzothienyl)ethyl]-1,4-diazabicyclo[2.2.3]nonane.

6. The compound of claim 3, which is 4-[2-naphthylethyl]-1,4-diazabicyclo[2.2.3]nonane.

7. A pharmaceutical composition comprising a therapeutically-effective amount of a compound, or pharmaceutically acceptable salt thereof, active for treating or preventing a CNS-related disorder selected from the group consisting of cerebral ischemia, a psychotic disorder and a convulsive disorder and a pharmaceutically acceptable carrier or diluent, wherein said compound or pharmaceutically acceptable salt thereof is selected from a family of compounds having the formula:

19

[Chemical structure diagram showing a molecule with substituents R, R¹, R², R³, R⁴, R⁵, R⁶, R⁷, R⁸, R⁹, R¹⁰, R¹¹, R¹², R¹³, A, (C)ₙ, and two N atoms]

wherein:

n is an integer of from 2 to 5;

R, $R^1$, $R^4$, $R^5$, $R^6$ and $R^7$ are independently selected from the group consisting of hydrido, loweralkyl, haloloweralkyl, and benzyl;

$R^2$, $R^3$, and $R^{10}$ through $R^{13}$ are independently selected from the group consisting of hydrido, hydroxy, loweralkyl, haloloweralkyl, benzyl, phenoxy, and benzyloxy;

$R^8$ and $R^9$ are independently selected from the group consisting of hydrido, loweralkyl, haloloweralkyl and benzyl; and A is selected from the group consisting of phenyl, naphthyl, benzothienyl, benzofuranyl and thienyl wherein any of the foregoing A groups can be further substituted with one or more substituents independently selected from hydrido, hydroxy, halo, loweralkyl, haloloweralkyl, loweralkoxy, amino, monoloweralkylamino and diloweralkylamino;

or a pharmaceutically acceptable salt thereof.

8. The pharmaceutical composition of claim 7, wherein:

n is an integer of from 2 to 5;

R, $R^1$, $R^4$, $R^5$, $R^6$, and $R^7$ are each independently selected from the group consisting of hydrido, hydroxy, methyl, ethyl, propyl, haloloweralkyl, and benzyl;

$R^2$, $R^3$, and $R^{10}$ through $R^{13}$ are each independently selected from the group consisting of hydrido, hydroxy, methyl, ethyl, propyl, haloloweralkyl, benzyl, phenoxy, and benzyloxy;

$R^8$ and $R^9$ are each independently selected from the group consisting of hydrido, methyl, ethyl, propyl, haloloweralkyl, and benzyl;

A is selected from the group consisting of phenyl and naphthyl; wherein any of the foregoing A groups can be further substituted with one or more substituents independently selected from the group consisting of hydroxy, methyl, ethyl, propyl, methoxy, ethoxy, methylenedioxy, halo, trifluoromethyl, amino, methylaminol and dimethylamino; or a pharmaceutically acceptable salt thereof.

9. The pharmaceutical composition of claim 8, wherein the compound is selected from the group consisting of:

4-[2-(3,4-dichlorophenyl)ethyl]-1,4-diazabicyclo[2.2.3]nonane;

4-[2-(3-benzothienyl)ethyl]-1,4-diazabicyclo[2.2.3]nonane;

4-[2-naphthylethyl]-1,4-diazabicyclo[2.2.3]nonane;

4-[2-(3,4-dichlorophenyl)ethyl]-1,4-diazabicyclo[3.2.3]decane;

20

4-[2-(3-benzothienyl)ethyl]-1,4-diazabicyclo[4.2.3]undecane; and

4-[2-naphthylethyl]-1,4-diazabicyclo[5.2.3]dodecane.

10. The pharmaceutical composition of claim 9, wherein said compound is 4-[2-(3,4-dichlorophenyl)ethyl]-1,4-diazabicyclo[2.2.3]nonane.

11. The pharmaceutical composition of claim 9, wherein said compound is 4-[2-(3-benzothienyl)ethyl]-1,4-diazabicyclo[2.2.3]nonane.

12. The pharmaceutical composition of claim 9, wherein said compound is 4-[2-naphthylethyl]-1,4-diazabicyclo[2.2.3]nonane.

13. A method for treating a patient afflicted with or susceptible to a CNS-related disorder selected from the group consisting of cerebral ischemia, a psychotic disorder, and a convulsive disorder, which method comprises administering to said patient a therapeutically-effective amount of a pharmaceutical composition containing an active compound or pharmaceutically acceptable salt thereof which is selected from the family of compounds having the following formula:

[Chemical structure diagram showing a molecule with substituents R, R¹, R², R³, R⁴, R⁵, R⁶, R⁷, R⁸, R⁹, R¹⁰, R¹¹, R¹², R¹³, A, (C)ₙ, and two N atoms]

wherein:

n is an integer from 2 to 5;

R, $R^1$, $R^4$, $R^5$, $R^6$ and $R^7$ are independently selected from the group consisting of hydrido, loweralkyl, haloloweralkyl, and benzyl;

$R^2$, $R^3$, and $R^{10}$ through $R^{13}$ are independently selected from the group consisting of hydrido, hydroxy, loweralkyl, haloloweralkyl, benzyl, phenoxy, and benzyloxy;

$R^8$ and $R^9$ are independently selected from the group consisting of hydrido, loweralkyl, haloloweralkyl and benzyl, and A is selected from the group consisting of phenyl, naphthyl, benzothienyl, benzofuranyl, and thienyl, wherein any of the foregoing A groups can be further substituted with one or more substituents independently selected from hydrido, hydroxy, halo, loweralkyl, haloloweralkyl, loweralkoxy, amino, monoloweralkylamino, and diloweralkylamino; or a pharmaceutically acceptable salt thereof.

14. The method of claim 13 wherein:

n is an integer of from 2 to 5;

R, $R^1$, $R^4$, $R^5$, $R^6$, and $R^7$ are each independently selected from the group consisting of hydrido, methyl, ethyl, propyl, haloloweralkyl, and benzyl;

$R^2$, $R^3$, and $R^{10}$ through $R^{13}$ are each independently selected from the group consisting of hydrido, hydroxy, methyl, ethyl, propyl, haloloweralkyl, benzyl, phenoxy, and benzyloxy;

$R^8$ and $R^9$ are each independently selected from the group consisting of hydrido, methyl, ethyl, propyl, haloloweralkyl, and benzyl;

A is selected from the group consisting of phenyl and naphthyl; wherein any of the foregoing A groups can be further substituted with one or more substituents independently selected from the group consisting of hydroxy, methyl, ethyl, propyl, methoxy, ethoxy, methylenedioxy, halo, trifluoromethyl, amino, methylamino, and dimethylamino; or a pharmaceutically acceptable salt thereof.

15. The method of claim 14, wherein the compound is selected from the group consisting of:

4-[2-(3,4-dichlorophenyl)ethyl]-1,4-diazabicyclo[2.2.3]nonane;

4-[2-(3-benzothienyl)ethyl]-1,4-diazabicyclo[2.2.3]nonane;

4-[2-naphthylethyl]-1,4-diazabicyclo[2.2.3]nonane;

4-[2-(3,4-dichlorophenyl)ethyl]-1,4-diazabicyclo[3.2.3]decane;

4-[2-(3-benzothienyl)ethyl]-1,4-diazabicyclo[4.2.3]undecane; and

4-[2-naphthylethyl]-1,4-diazabicyclo[5.2.3]dodecane.

16. The method of claim 15, wherein said compound is 4-[2-(3,4-dichlorophenyl)ethyl]-1,4-diazabicyclo[2.2.3]nonane.

17. The method of claim 15, wherein said compound is 4-[2-(3-benzothienyl)ethyl]-1,4-diazabicyclo[2.2.3]nonane.

18. The method of claim 15, wherein said compound is 4-[2-naphthylethyl]-1,4-diazabicyclo[2.2.3]nonane.

19. The method of claim 13 wherein said CNS-related disorder is cerebral ischemia.

20. The method of claim 13 wherein said CNS-related disorder is a psychotic disorder.

21. The method of claim 13 wherein said CNS-related disorder is a convulsive disorder.

* * * * *